(12) United States Patent
Roser

(10) Patent No.: US 7,798,645 B2
(45) Date of Patent: Sep. 21, 2010

(54) VISUAL AND MEMORY STIMULATING RETINA SELF-MONITORING SYSTEM

(76) Inventor: Mark Costin Roser, 515 Old Slocum Rd., Hebron, CT (US) 06248

( * ) Notice: Subject to any disclaimer, the term of this patent is extended or adjusted under 35 U.S.C. 154(b) by 378 days.

(21) Appl. No.: 11/803,648

(22) Filed: May 15, 2007

(65) Prior Publication Data

US 2007/0268455 A1 Nov. 22, 2007

Related U.S. Application Data

(60) Provisional application No. 60/800,614, filed on May 16, 2006.

(51) Int. Cl.
*A61B 3/02* (2006.01)
*A61B 3/00* (2006.01)
(52) U.S. Cl. ...................... 351/223; 351/200
(58) Field of Classification Search .............. 351/200, 351/222–223
See application file for complete search history.

(56) References Cited

U.S. PATENT DOCUMENTS

| | | |
|---|---|---|
| 5,589,897 A | 12/1996 | Sinclair |
| 5,618,673 A | 4/1997 | Narang |
| 5,789,653 A | 8/1998 | Skarnes |
| 5,838,422 A | 11/1998 | Caskey |
| 5,946,075 A | 8/1999 | Horn |
| 6,010,860 A | 1/2000 | Bushman |
| 6,033,858 A | 3/2000 | Bastian |
| 6,329,179 B1 | 12/2001 | Kopreski |
| 6,585,376 B1 | 7/2003 | Matsumoto |
| 6,656,131 B2 | 12/2003 | Alster |
| 7,166,079 B2 | 1/2007 | Febbrofiello |
| 2005/0122477 A1* | 6/2005 | Alster et al. ................ 351/237 |

FOREIGN PATENT DOCUMENTS

| | | |
|---|---|---|
| WO | WO 97/35589 | 10/1997 |
| WO | WO 98/14617 | 4/1998 |
| WO | WO 00/65357 | 2/2000 |
| WO | WO 02/079511 A1 | 10/2002 |

OTHER PUBLICATIONS

Schuchard, Ronald, Validity and Interpretation of Amsler Grid Reports, Arch Ophthalmol—Jun. 1993; 776-780; vol. 111.
Achard, Oliver, Role of the Completion Phenomenon in the Evaluation of Amsler Grid Results, Am Journ of Ophthalm, 1995;120:322:329.
Zaidi, FH; The Amsler Chart is of Doubtful Value . . . ; Eye; 2004; 503-508; vol. 18; Nature Publishing Group.
Loewenstein, Anat; Replacing the Amsler Grid; Ophthalmology; May 2003; 966-971; vol. 110.
Zur, Dror, Filling-in of Retinal Scotomas; Vision Research; 2003; 971-982; vol. 43.
Oliver-Fernandez, Alejandro; Progression of Visual Loss and Time Between Initial Assessment and Treatment of Wed AMD; Canadian J Ophth; 2005; 313-319; vol. 40.

(Continued)

*Primary Examiner*—Scott J Sugarman
*Assistant Examiner*—Dawayne A Pinkney

(57) ABSTRACT

A system is described for objective patient self-testing and time-based self-monitoring of retina diseases that improves quality, usability and confidence compared to currently available testing options.

12 Claims, 2 Drawing Sheets

OTHER PUBLICATIONS

Augustin, AJ; Comparison of the Original Amsler Grid with Modified . . . ; Retina; Jun. 2005; 443-445; vol. 25(4).

Crossland, M; The Amsler Chart: absense of evidence is not evidence of absence; Br. J Ophthalmol; Mar. 2007; 391-393; vol. 91(3).

Diatchenko, L. et al., "Suppression subtractive hybridization: A method for generating differentially regulated or tissue-specific cDNA probes and libraries;" Jun. 1996; *Proc. Natl. Acad. Sci. USA*, vol. 93; pp. 6025-6030.

Kopreski, Michael S., et al., "Detection of Tumor Messenger RNA in the Serum of Patients with Malignant Melanoma;" Aug. 1999; *Clinical Cancer Research*; vol. 5; pp. 1961-1965.

Schena, M., "Genome Analysis with Gene Expression Microarrays;" 1996; *BioEssays*; vol. 18; pp. 427-431.

Theil, D., et al., "Nuclear DNA Fragmentation and Immune Reactivity in Bovine Spongiform Encephalopathy;" 1999; *J. Comp. Path.*; vol. 121; pp. 357-367.

*The New Encyclopaedia Britannica*; 1994; 15th Edition; vol. 25; p. 912.

Van Keulen, L.J.M., et al., "Diagnosis of Bovine Spongiform Encephalopathy: A Review;" Oct. 2000; *The Veterinary Quarterly*; vol. 22; No. 4; pp. 197-200.

Yershov, Gennady, et al., "DNA Analysis and Diagnostics on Oligonucleotide Microchips;" May 1996; *Proc. Natl. Acad. Sci. USA*; vol. 93; pp. 4913-4918.

Brenig, B. et al., "Cellular nucleic acids in serum and plasma as new diagnostic tools;" Mar. 2002; *Berliner und Münchener Tierärztliche Wochenschrift*, vol. 115; pp. 122-124.

Dandoy-Dron, F., et al., "Enhanced levels of scrapie responsive gene mRNA in BSE-infected mouse brain;" Mar. 2000; *Molecular Brain Research*; vol. 76; pp. 173-179.

Gibson, Toby J., "RuNAway Disease: A two cycle model for transmissible spongiform encephalophathies (TSEs) wherein SINE proliferation drives PrP overproduction;" Jun. 2001; *Genome Biology (Online)*; vol. 2; pp. 6.1-6.17.

Hochstrasser, D., et al., "Elevation of apolipoprotein E in the CSF of cattle affected by BSE;" Oct. 1997; *FEBS Letters*; vol. 416; pp. 161-163.

Ramsay, Graham, "DNA Chips: State-of-the-art;" Jan. 1998; *Nature Biotechnology*; vol. 16; pp. 40-44.

Riemer, C., et al., "Identification of upregulated genes in scrapie-infected brain tissue;" Nov. 2000; *J. of Virology*; vol. 74; pp. 10245-10248.

\* cited by examiner

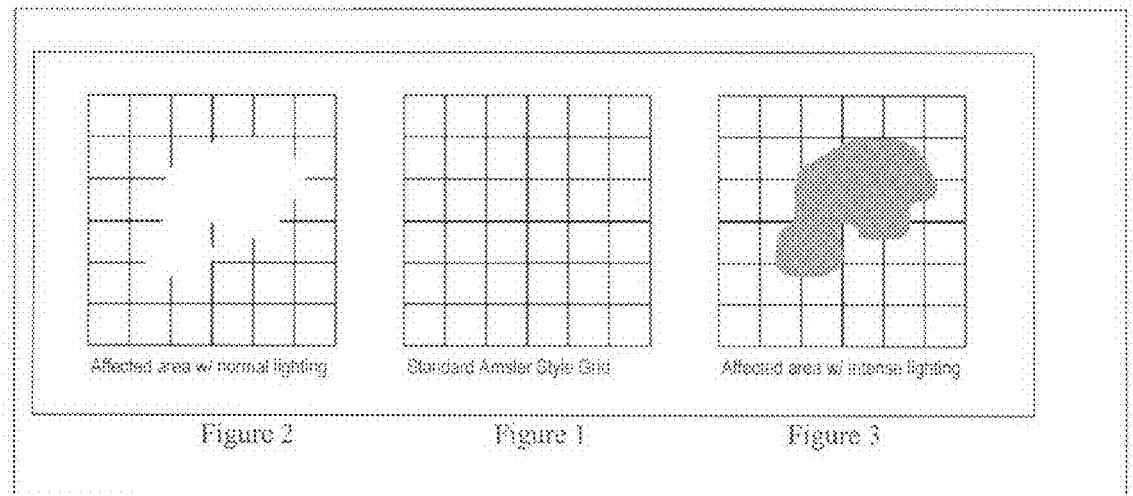

Figure 2 — Affected area w/ normal lighting
Figure 1 — Standard Amsler Style Grid
Figure 3 — Affected area w/ intense lighting

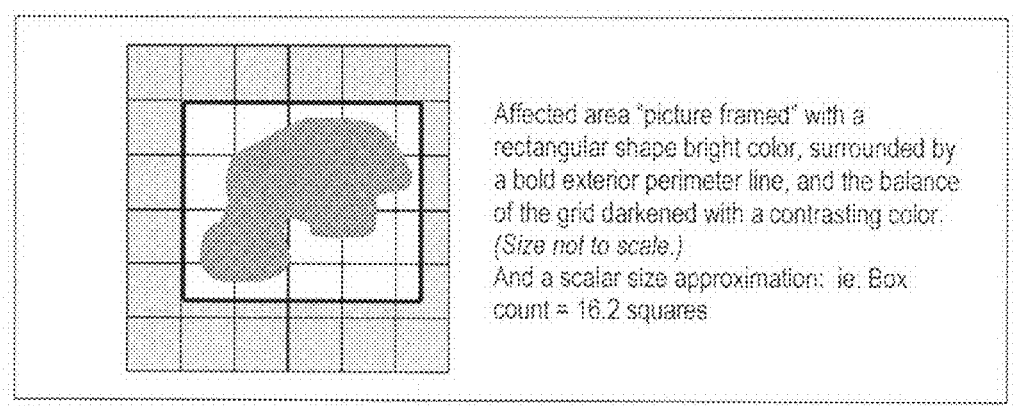

Affected area "picture framed" with a rectangular shape bright color, surrounded by a bold exterior perimeter line, and the balance of the grid darkened with a contrasting color. (Size not to scale.)
And a scalar size approximation: ie. Box count = 16.2 squares

Figure 4

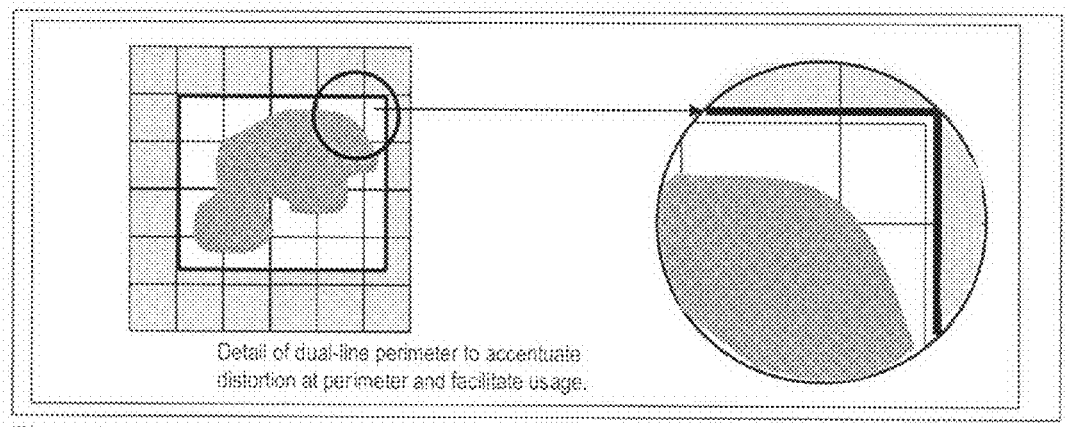

Detail of dual-line perimeter to accentuate distortion at perimeter and facilitate usage.

Figure 5

VISUAL AND MEMORY STIMULATING RETINA SELF-MONITORING SYSTEM

CROSS-REFERENCE TO RELATED APPLICATIONS

This document follows upon Provisional 60/800,614 dated May 16, 2006 by Mark Costin Roser.

BACKGROUND OF THE INVENTION

Age-related macular degeneration (AMD) is the major cause of irreversible legal blindness in the western world. Over 12 million Americans have some type of AMD, with millions of other suffering from other retina issues. Current self-monitoring tools for retina diseases fail to adequately indicate the need for treatment, resulting in delayed treatment starts and higher incidences of severe vision loss. These inventions will boost patients' ability to accurately and confidently self-monitor their vision between office visits resulting in fewer people losing their sight.

The Amsler and Yanuzzi grids, the only widely used self-tests for AMD, have proven largely ineffective at enabling patients to recognize the signs that they should consult their retina specialist for treatment. There are no other commonly available tools for patient self-monitoring in one's home between office visits. The Amsler Grid has been in use and largely unchanged for more than 60 years. Shortcomings of the Amsler grid include but are not limited to: periodicity of the test pattern, lack of individual adjustment, lack of visual & memory stimulating triggers, inability to overcome the visual completion phenomenon, poor compliance, subjectivity, lack of quantification, anxiety and doubt, relatively high levels of concentration required and habituation.

While the dry form of AMD progresses slowly over years, the wet form of AMD progresses rapidly and can mature from a nascent stage to legal blindness in fewer than 12 months. Thus, annual vision check-ups are not sufficient to protect patient's visual health; and accurate self-monitoring is essential. However, the current grid tests do not provide accurate self-monitoring. The result is that many people are needlessly suffering advanced vision loss and blindness because they lack the ability to accurately and confidently monitor their vision and know when to accelerate their visit to their eye care professional before their scheduled appointment date.

There have been great strides in research and treatment over the past 5 years. New treatments such as drug therapy (VEGF treatments such as Macugen® from Eyetech/Pfizer and Lucentis® from Genentech) and photodynamic therapy now add significant mechanisms to the available armamentarium of care. These new treatments, however, are most effective when they treat problems in the early stages. For them to be most effective—there must be a reliable means of detecting problems such as metamorphopsia and onset of new blood vessel growth early. Delay in the start of any retina treatment can greatly limit the eventual outcome. Efficacy of drug treatment declines according to the progression of the disease; too much delay greatly increases the likelihood of vision loss and blindness.

In clinical testing, the Amsler grid has not proven successful at enabling patients to detect issues nor to understand when to seek council of their retina specialist. The following references are made to the scientific literature:

Referencing: Schuchard, Arch. Ophthalm 1993 vol 111 no. 6
"For scotomas of 6 degrees or less in diameter, 77% of standard and 87% of threshold scotomas were not detected by Amsler grid testing." "Amsler Grid reports have poor validity and cannot be accurately interpreted for use in the clinical diagnosis of retinal defects."

Zaidi, et al, Eye, May, 2004—
"The surveillance protocol detected less than 30% of the specific patients who subsequently underwent laser treatment." "Bearing in mind the prevalence of AMD and the increased therapeutic importance of early detection of SRN, it is clear that improvements in the current surveillance protocol are required."

Achard, et al, Am J. Ophthalmol. 1995—
"Results of two successive Amsler grid tests were not comparable, even when the technique was identical and time between tests was no more than 2 to 15 min." "the Amsler grid technique is unreliable for evaluating central scotomas."

A variety of reasons have been put forward by these studies to explain the reasons behind the poor performance of the Amsler grid:

Schuchard, Arch. Ophthalm 1993 vol 111 no. 6
"The perceptual filling-in of patterns such as the Amsler grid and fixation characteristics have a major influence in the result of Amsler grid testing."

Zaidi, et al, Eye, May, 2004—
" . . . difficulty with compliance . . . ", " . . . problems with the subjective nature of the test.", "Relatively high levels of concentration are needed to undertake the test . . . ", " . . . levels of fatigue and anxiety are important,", " . . . compounded by the perceptual completion phenomenon . . . "

Achard, et al, Am J. Ophthalmol. 1995—
"Our data corroborated Schuchard's observations regarding the relatively poor sensitivity of Amsler grid tests.", "Additionally, our study further characterized the completion phenomenon found when Amsler grid tests are used and emphasized the rapid changes that occur in completion over time.", "It cannot be excluded that the changes in results over time were partly because of changes in fixation position."

This research is corroborated by the inventor's general conversation with retina patients. In interviews, the following assertions are supported by patient anecdotes:

1. Poor compliance with test protocol—many neglect to do any testing
2. Confusion regarding purpose—many did not know why they were given the Amsler
3. Confusion regarding baseline & monitoring—none knew they were supposed to monitor their vision over time
4. Confusion regarding proper usage—several reported looking for "moving" or "changing" lines as if they expected to see motion on the card as the symptom of further disease In the inventor's personal experience as a wet AMD patient for over 10 years, the Amsler grid has shortcomings in further areas, including but not limited to:

1. Difficulty in detecting changes to vision especially subtle changes
2. Difficulty in locating the periphery of the affected, scarred or damaged retinal area
3. Difficulty in detecting changes to the size or complexion of an affected area
4. Difficulty in establishing a benchmark viewing distance
5. Difficulty in locating and/or maintaining a gaze at the center of a grid without wandering
6. Difficulty in remembering the exact limits of an affected area The impact of these diagnostic shortcomings include but are not limited to:
1. Substandard identification of newly affected areas (of the retina)
2. Incorrect or missing identification of newly affected areas
3. Substandard assessment of size and complexion of affected areas
4. Lack of confidence in daily measuring
5. Frustration with the assessment process
6. Variation in day-to-day assessment of the overall size and complexion of an affected area The result and consequences of these impacts include but are not limited to:
1. Unnecessary delays in reporting to retina specialists resulting from lack of confidence in one's self assessment of visual loss (ie: patients fail to present because of internal doubt that could be personified by the following fictional self-talk dialogue: "Am I sure that my vision was truly different last week, who am I to make such a diagnosis?")
2. Missed detection of problems at their onset
3. Delays of days/weeks/months/years before problems are identified (either because the problem is finally impacting routine daily visual activities or problem is finally identified by a healthcare professional)
4. Unnecessary delay in start of treatment (delay in presenting promptly delays start of treatment) thereby diminishing the likelihood of optimum treatment effectiveness
5. Unnecessary sense of anxiety & frustration resulting from not knowing the status of one's eye health between office visits (ie: am I losing my vision?)
6. Emotional consequence of feeling helpless and unable to participate in disease management
7. Poor compliance with regular monitoring of existing problems
8. Higher likelihood of vision loss The implication to the drug industry are many:
1. Fewer patients receive treatment at the earliest stages of disease
2. Fewer patients fall within the treatable range of the disease because many have progressed beyond acceptable treatable limits
3. More patients fail to receive full benefit of their treatment, some find the treatment ineffective because they started late, and many lose significant vision
4. The drug and class of drugs does not get as good of a reputation if compared to a scenario where all patients reported onset days or weeks earlier
5. Sales of drugs suffer
6. Marketing budgets may need to be increased to compensate for lack of "word of mouth"

Societal implications include, but are not limited to:
1. Vision loss directly reduces a patient's ability to be a productive contributor to society
2. Vision loss indirectly taps patient's family's ability to productively contribute to society
3. Vision loss increases the need for social services and other governmental support
4. Delayed presentation increases the extent of drug/PDT/laser treatment required, increasing the monetary costs through public & private insurance programs I feel strongly that the novel ideas and approaches enclosed will benefit others by giving them more accuracy, simplicity and ease in the monitoring of their vision. As a result, monitoring will be performed more regularly, with better adherence and higher accuracy and confidence. And thus, any necessary treatments will be delivered as soon as practical thereby increasing the chances for best treatment results and reducing the risk of vision loss and blindness.

Definitions:

By the term "affected area"—I mean to describe any type of disturbance to the retina—whether the result of dry macular degeneration, wet macular degeneration, diabetic retinopathy, toxic histoplasmosis, scarring from light or laser, blind spots (scotomas), etc. These words will be used to describe the disturbance in any phase of progression from onset through maturity, pre and post treatment.

I will use the terms "person", "patient", "user" and "people" all interchangeably. It is not my intent to limit the inventions by narrowing their use to any particular population. These inventions are valuable to all people in any state of health or with any type of eye disorder (save total blindness).

By the term "grid test"—I mean tests such as the Amsler test that are commonly known in the ophthalmology field for detecting the presence of retina disturbances, detecting the size and shape of the affected part of a patients visual disturbance, and through a protocol of monitoring over time, detecting changes to the size and/or shape of the affected area.

By the term "visually stimulating grid"—I mean a grid test that has sufficient differentiation in the qualities of the lines within the grid to enable a patient to recall (verbally or through manually pointing) the difference between one line and the neighboring parallel line (which stands in contrast to traditional grid tests which have ostensibly identical lines that are difficult to differentiate and thus difficult to recall).

By the term "plurality of distinguishably different lines"—I mean that at least four or more lines within the grid are differentiated from the other lines in the grid through the use of color, dash or dot line patterns, line weight (aka: stroke or boldness), double lining (aka: very proximate parallel lines), or a combination of these approaches.

By the term "orientation of the distinguishably different lines"—I mean that the plurality of distinguishably different lines are organized in the grid in a way that is perceived by users to be a pattern and not as a discordant or chaotic layout, which implies a the layout to be congruous with any commonly understood visual pattern, such as symmetry, concentricity, progression, among others.

By the term "indicia"—I mean the use of letters & numbers to represent the pattern of lines within a grid test, one embodiment of which would be latitude & longitude markings of "Up 1", "Up 2", etc.

By the term "illuminance threshold"—I mean the point at which a grid test's surface illuminance stands in proper differentiation to the illuminance of the surrounding area so that a patient's affected area appears more pronounced because the "filling-in phenomenon" is partially over-ridden.

By the term "outer limit perimeter line"—I mean a line that is created immediately beyond the limits of a patient's affected visual area, and thereby establishes a surrogate manner of measuring the size & shape of a patient's affected visual area at a given moment in time.

By the term "results of the size and shape of the outer limit perimeter line test"—I mean both the quantifiable measurements of perimeter geometry (such as height×width and an anchor location in the x/y plane) as well as well as the qualitative memory of the size and shape of a patient's affected area.

By the term "pairing of at least two parallel lines"—I mean that lines can be intentionally drawn parallel to each other and separated by a space equal to 1× to 8× the stroke width of the line.

By the term "surface area outside of the perimeter"—I mean the surface area of a grid test that lies outside the surface area of the shape that defines the perimeter.

By the term "poor compliance"—I mean a patient's failure to use a test on a regular basis over days, weeks and months which leads to an inability to track vision loss over time.

By the term "subjectivity of the test"—I mean a lack of ability within the test that would enable consistent measurements over weeks and months of usage.

By the term "lack of quantification"—I mean the lack of patients' ability to remember the extent and shape of a visual distortion or scotoma at a given time.

By the term "anxiety"—I mean that patients who are experiencing visual challenges are under emotional strain and the lack of consistent self-monitoring measurements can exacerbate this state of emotional unrest, and especially a heightened fear of impending blindness.

By the term "doubt"—I mean that patients who are unable to have confidence in the measurement of their vision often don't know whether to attribute a change in their vision to a progression of their disease or consider it within the limits of their test.

By the term "relatively high levels of concentration required"—I mean the lack of proper visual and memory stimulus in Amsler grids places high demands on the patient to maintain concentration.

By the term "habituation"—I mean that patients using the Amsler grid "get used" to seeing distortions and reduces ability to detect and differentiate changes over longer time intervals.

I will use the words "changes to vision", "metamorphopsia", and "changes to affected area" very loosely and often interchangeably.

I will use the terms "earliest stages of disease" and "onset of issues" very loosely and often interchangeably. I will use the terms "adherence", "compliance and "persistence" very loosely and often interchangeably. These terms are used thusly because a general usage does not have a material impact on the nature of the inventions.

By the term "Visual completion phenomenon" (aka the "filling in phenomena")—I mean that the brain working together with the eyes is able to fill-in and approximate areas of missing vision and thus makes proper visualization of the size and shape of an affected area of the visual field (such as a scotoma) difficult, less accurate and less able to track over months & years of time Expanding Upon the "Visual Completion Phenomenon":

As we know from clinical research and personal experience, vision is based on the brain's interpretation of visual data from the eyes. Thus, "vision" is comprised of both an "optical-sensory" component and a "cognitive" component. Metaphorically speaking: V (vision)=OS (optical sensory)+C (cognitive). Tests of acuity and grid reading, therefore, reflect both the patient's optical-sensory performance and cognitive abilities.

In measuring the progression of macular degeneration and other retinal illnesses, our prime concern is on the condition and health of the optical-sensory components of vision and their ability to perform. Measuring their performance, however, must be done in recognition that the cognitive process is not a constant. Metaphorically speaking: OS (optical sensory)=V (vision)−C (cognitive).

Especially in cases of eye disease, the cognitive process is boosted into a highly active state to help compensate for the optical-sensory deficiencies. This being the case, we must understand ways to over-ride the cognitive manipulation of optical sensory data or to normalize the cognitive manipulation during times of measurement to a constant value.

Whether we know it or not, each of us has two blind spots (aka "affected areas") in our vision. The optic nerve passes through each of our retinas, creating small areas devoid of rods and cones. This results in an actual blind spot in each of our eyes. However, because of the cognitive process, the great majority of people will go through life and never know that they have these "holes" in their vision Why? Because the brain takes the visual data surrounding the affected area and then "fills in the hole" with what it considers to be the best match. The same thing happens with retinal scars or affected areas.

So, if you are looking at a yellow wall, the brain instantly "fills in" the affected area with the same yellow color. If you are looking at a black wall, the brain instantly "fills in" the affected area with the same black color. And amazingly, if you are looking at a pattern, the brain continues the pattern over the affected area. This applies to the grid tests as well, and complicates the measuring of affected areas.

Impact of the "Filling-In Phenomenon":

Grid tests are based on the assumption that scarred or damaged areas will show up as "holes" or wavy lines on the grid. Unfortunately, the cognitive process extrapolates the grid and attempts to fill in the hole by continuing the grid pattern in the affected area—especially around the edges. This makes these tests frustrating and reduces their accuracy.

Thus, grids are all limited in their ability to function based upon their inability to differentiate what part of the perceived image is due to the cognitive process and what part of the perceived image is due to the optical sensory visual output of the eyes.

Over-Riding the Cognitive Process to Help Improve Measurement:

While the brain attempts to compensate for 100% of the affected area, it has its limitations. By exceeding these limitations, we can isolate the effects of the cognitive process and better measure the sensory-visual performance.

From my experience, the brain is limited in three major areas in its ability to "fill-in" an affected area:
1. Non-continuous patterns
2. Very bright objects or surfaces
3. Discontinuously dynamic objects (moving, flashing, color shifting or changing in a meaningful way)

By employing some/all of these into a testing protocol, we are able to help the user understand when their vision is being impacted by the filling-in phenomenon.

BRIEF SUMMARY OF THE INVENTION

The inventor has developed multiple versions of improved test grids, both static and dynamic, that are designed to stimulate visual and memory cues, facilitate monitoring of one's vision over time and allow for personal customization.

BRIEF DESCRIPTION OF THE SEVERAL VIEWS OF THE DRAWING

FIG. 1 shows a standard Amsler style grid.

FIG. 2 shows a representation of how this standard grid is perceived (by a patient with an affected area) under normal task lighting general embFIG. 3 shows a representation of how this standard grid is perceived (by a patient with a affected area) while above the illuminance threshold.

FIG. 4 shows an affected area "picture framed" by an approximate outer limit perimeter line. The size and shape of this outer limit perimeter line acts as a surrogate for the actual size and shape of the affected area. The ease of use of the outer limit perimeter line is also improved through the use of a bright hue within the picture frame and the balance of the grid darkened by a contrasting color. The perimeter was defined by "stretching the four sides" of a rectangle such that the edges are close to the affected area but so close that they get distorted. The resulting area is calculated as a scalar value based upon surface area of the picture frame.

FIG. 5 shows detail of one iteration of the borderline of a picture frame. In this iteration, the borderline has a bold line (=2 to 3× stroke of the conventional grid lines) with a secondary line of narrow stroke (=roughly ½ stroke of the conventional grid lines) separated by the width of the bold stroke line. Distortion is more easily detected in this configuration because the two parallel lines tend to bleed together and the confluence of the lines is a highly visible "vee" shape.

2—orientation of the said plurality of distinguishably different lines such that they are symmetric in their reference to the center dot (ie: blue dotted line, then black line, then bold black dotted line, then red line, then black dashed line, then bold green line, then black line.) in such a way as to show a pattern 3—indicia that are associated with each of the lines of the grid that complement the orientation of the lines and reinforce its pattern Note: the gray curved shape in the drawing is to symbolize an example of patient's vision loss as the result of AMD

DETAILED DESCRIPTION OF THE INVENTION

Figure 6:
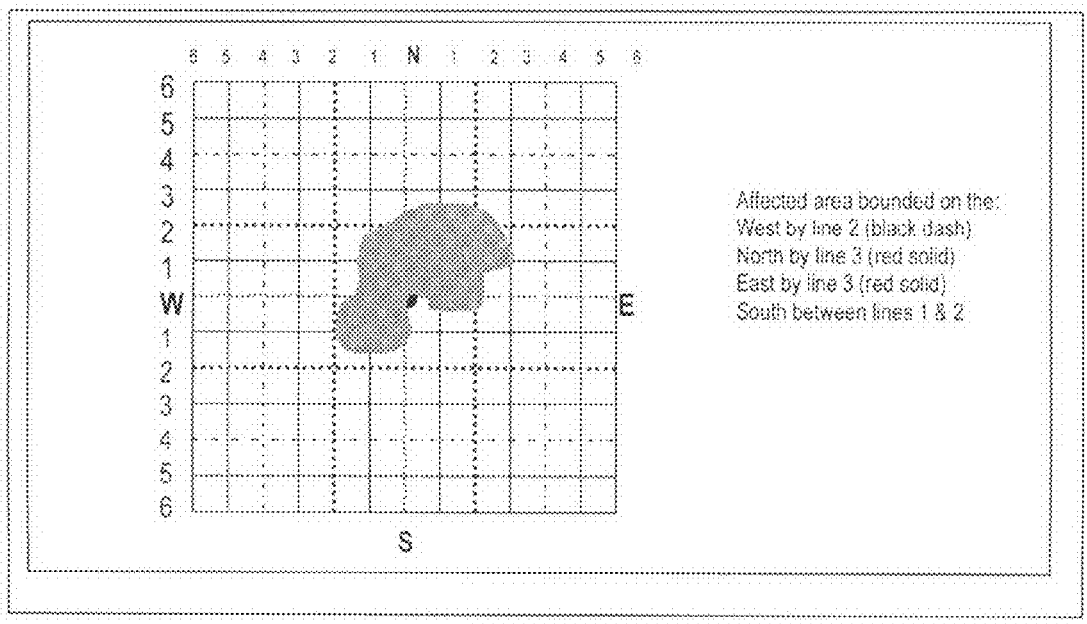
FIG. 6 shows several design features of the visually stimulating grid system, including 1—a plurality of lines that are distinguishably different from the other lines in the grid (through color, line weight & dot-dash)
Figure 7:
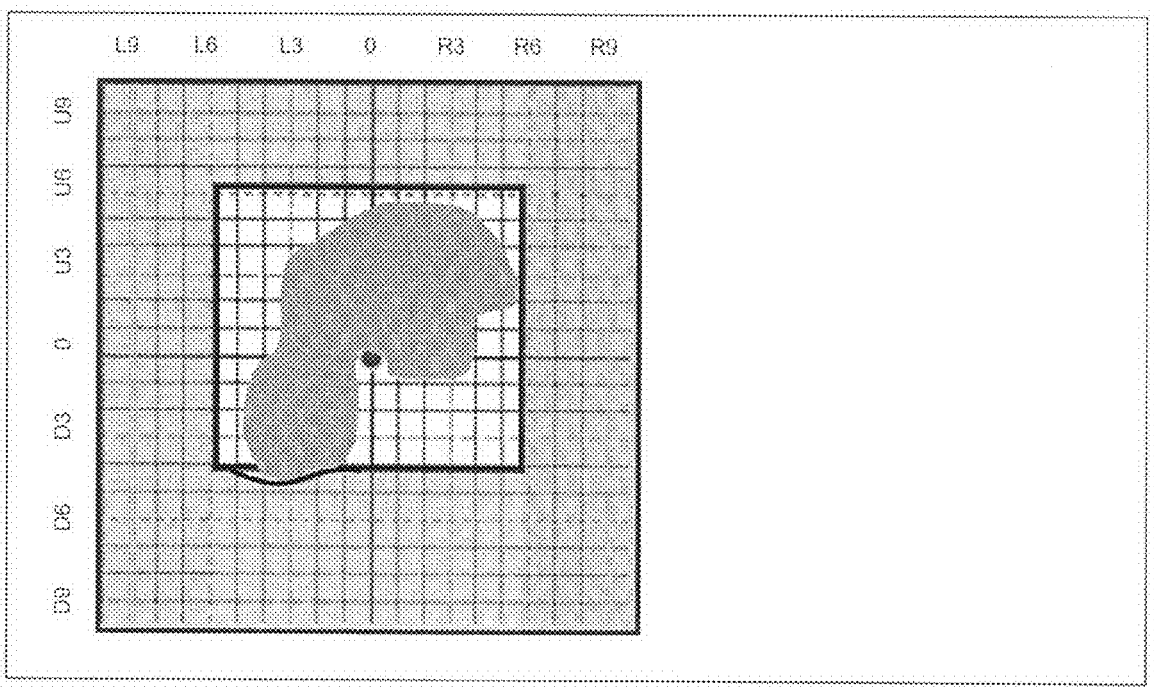
FIG. 7 shows an illustration of what a patient might notice if the size and or shape of their affected area grows and thereby exceeds the limits of the baseline picture frame.

The reasons for problems with the existing grids are numerous, and are addressed by the following inventions.

Improving visual stimulation through distinguishably different lines and the orientation of said lines:

Current grid tests have lines that are ostensibly identical to each other. When a patient uses such a grid test, they must notice the limits of their visual loss, which are typically in their peripheral vision. By definition, they cannot directly look at or gaze at the outer edge of their affected area, they must use their peripheral vision and "notice" where the limits of the affected area are.

Without any differentiation of the lines in the grid, it is very difficult and very subjective to associate a particular grid line with the outer limit of one's affected area. To overcome this, the inventor has developed lines that are distinguishably different within the grid. This immediately provides visual stimulation that facilitates "noticing" which line was adjacent to the limit of one's affected area.

Orienting the lines in a way that establishes a sequence recognized as a pattern further facilitates "noticing" lines in peripheral vision. By orienting the distinguishably different lines into a sequence that is recognized as a pattern, the invention leverages commonly known patterns that are familiar to most patients and thus are pre-existent in their mind. This connection between the grid and the mind stimulates the mind and memory, thereby facilitating immediate recall, short-term recall and long-term recall. The grid is perceived as a distinct "landscape" that enhances cognitive interpretation regarding the limits of one's affected areas. Sequences that can be interpreted as patterns include:

1—Progression (having the increasingly dominant items emanate from a common base point)

2—Concentricity (using differentiated lines in the shape of a square that overlap existing grid lines in increasingly larger sizes (such as Russian dolls) centered around the center dot of the grid, ie: the first differentiated line based square overlaps the outer edge of the adjoining four grid squares (2×2) that surround the center dot of the grid, the next square overlaps the 36 grid squares (6×6) that surround the center dot of the grid, etc)

3—Symmetry (having the differentiated lines in a sequence that is consistent as it emanates from the center, for example black, blue, green-dashed, bold red sequence repeated going up, right, left and down away from the center dot)

Introducing Indicia to Label the Lines:

The lines may be labeled with indicia. The indicia can be labeled as a map is labeled with latitude and longitude numbering scheme to enhance patients' ability to remember the extent of their affected areas and to communicate them to others. Latitude and Longitude keys are typically noted to the outside perimeter of the grid. Patients can then look at the latitude and longitude for to help remember the rough size of their affected area, and to provide a common language between the patient and the caregiver. Without such indicia, the patient has very little vocabulary with which to communicate the limits of their affected area.

These improvements reduce the subjectivity of the tests and the effort associated with ongoing monitoring, both of which will help reduce problems associated with poor compliance. The ability to more confidently measure one's affected area also reduces the anxiety associated with not knowing the status of one's visual health.

Exceeding the Illuminance Threshold to Overcome the "Filling-in Phenomenon":

As mentioned previously, the brain "fills in" affected areas with approximations of the surrounding visual field. For example, while looking at a blue wall, the brain will "fill in" the affected area with the exact color, hue and saturation of blue—making the affected area unnoticeable to the person.

While the brain can easily match most colors in the visual field to fill-in an affected area, it is not capable of reproducing brightly illuminated surfaces. So, while the eye can seamlessly fill-in a affected area on a white sheet of paper under normal lighting, it cannot fill-in a affected area while looking directly at the surface of a fluorescent light fixture or the surface of a white sheet of paper held in the rays of a 100 watt desk lamp. I shall refer to this transition point the "illuminance threshold".

The transition from "normal" lighting to "very bright" surface is subjective and relative to many factors, including but not limited to: the brightness of the surrounding area, person's age, person's visual health, and time necessary for eyes to adjust from a light to dark surface. In indoor ambient home lighting of 25 to 40 fc (Or foot-candle, which is equivalent to approximately 10 lux), the transition can occur at approximately 100 to 150 fc. In bright sunlit indoor rooms of roughly 100 fc, this transition may be perceived at 150 to 300 fc or greater. In dimly lit indoor rooms of 5 to 20 fc, this transition may be perceived at 25 to 100 fc or less. A squint reaction is generally accepted to begin at approximately 350 fc after sustained exposure to bright light; and the same squint reaction can be experienced at 100 fc or less without exposure to light—as experienced after waking from sleep.

The threshold is subject to change from person to person and will be relative to the ambient light of the surrounding area wherever the person finds themselves as well as their time that they have spent in those conditions.

Once the light from the grid surface exceeds the illuminance threshold, the brain is no longer able to fully compensate for the affected area. The result is that the affected area now appears darker than the surrounding area and the actual shape and size of the affected area is dramatically easier to perceive. In other words, where a typical grid test results in an affected area being visualized by missing "negative space", surpassing the illuminance threshold results in the affected area showing up as a dark blob "positive object".

Thus, testing conditions should deliver grid brightness that exceeds the users' perceptions of their illuminance threshold for the environment in which they find themselves. In typically lit indoor rooms, grids should emit or reflect approximately more than 100 fc but less than 300 fc (to prevent squint reactions). (This illuminance will vary with room lighting, patient age, eye health and other factors.)

Under these circumstances, the affected area cannot match the intensity and therefore it shows up several shades darker than the illuminated background. This helps an edge to be more clearly defined and traced. The affected area's "shadow" also will tend to linger for a brief moment after looking away from the grid which helps the user to remember the size and shape of their area. This reduces the effort and concentration required to utilize the tests.

This makes many electronic displays ideal for this purpose. Displays such as CRT's, LCD's, DLP's, and other available electronic displays often emit or reflect light of sufficient luminance to exceed the illuminance threshold. Common home computer displays that do not have a very high luminance can be used by simply reducing the ambient light of the surrounding environment (waiting for dark, dimming lights, switching lights off, drawing curtains, etc).

Since the illuminance threshold is observable by retina patients, they can be given instructions on how to reduce their ambient lighting sufficiently to achieve the goal.

By driving the brightness of the grid through electronic display, one can also incorporate a defined user interaction to ensure brightness surpasses the illuminance threshold. By asking the user questions to which they can respond yes/no, a software based application can test whether the display brightness is surpassing the threshold. If so, the user is ready to perform their testing/monitoring with the grid. If not, the application can increase brightness of the screen (with software controllable screens), can instruct the user to boost the brightness of their screen (with user controlled buttons & knobs if available), and/or can instruct the user to dim the environmental lighting, or can instruct the user to wait until they are in a darkened space. This control over brightness, in conjunction with interactive feedback from the user—helps ensure that the appropriate luminance is delivered relative to the environmental conditions and/or that the environmental conditions are (or become) modified prior to testing/monitoring.

Discontinuously Dynamic Objects:

The brain requires a certain time to compensate for the affected area. By using a discontinuously dynamic object (such as a blinking line, a marquis style progression of dots along a line, a wiggling line, etc), the brain is less likely to be able to approximate or fill in the activity of the object.

By constructing a grid with a number of discontinuously dynamic lines, the edge of the affected area is easier to determine.

"Picture Framing" with an Outer Limit Perimeter Line

Many patients are frustrated by trying to maintain a fixed gaze at a center dot. For example, people with a limited or no central vision remaining, there is a large struggle to maintain their gaze on the center. Without this central benchmark, it is very easy for the eye to wander and very difficult to obtain a consistent evaluation of the affected area. This leads to poor results, frustration and lack of adherence to regular monitoring.

For such people, and anybody who is not able to comfortably focus on the center dot, further enhancements can be made. Affected areas may be "picture framed" using any number of techniques to make a perimeter line that encompasses the outer limit of the affected area. By creating an outer limit perimeter line around the affected area that is slightly (approximately 1% to 50%) larger than the diameter of the affected area, an effective "picture frame" is created around the affected area. The person can then use the size and shape of this perimeter line to gain multiple benefits.

Perimeter reference points (ie: the external perimeter lines of the picture frame) enable the eye to reference a set of "fixed" objects that can act as a surrogate for a center dot which may be invisible to a person with no remaining central vision. Using the perimeter as reference points, they can better keep their gaze fixed and have a much improved ability to measure and monitor the size and shape of their affected area.

Establishing a perimeter that is just large enough to surround a patient's affected area, such that the outside perimeter border line is not distorted, ensures that the "picture frame" has encompassed the entire size of their impacted area. This can be confirmed by instructing the patient that any wandering of their gaze should never distort more than two adjacent picture frame lines. The dimensions of the size & shape of the picture frame then becomes a surrogate to the actual size and shape of the affected area.

Quantifying and Tracking the Size and Shape of the Outer Limit Perimeter Line:

These inventions are unique, in that they are intended to support absolute measurements performed in a clinical setting, but not replace them.

Their value is derived from their ability to measure changes to vision. Having an accurate understanding of change in vision is very valuable in alerting patients and caregivers that attention may be necessary. For example, if dry macular degeneration starts to transition to wet form, or if wet macular degeneration starts to affect a fellow eye in a unilateral MD patient, or if macular generation scotoma experiences metamorphopsia. In all these instances, an absolute vision measurement would not necessarily heighten the detection of change. Rather, it is the time based comparison of one measure against another measure (or set of measures) that distinguishes change. This can be accomplished by understanding the size and shape of the affected area at one point in time and comparing it to the size and shape at a later point in time. If the affected area has grown, it is a signal that there may be a growth of the affected area that may need treatment, and that the patient should visit their eye care professional right away, before their next scheduled office visit.

The use of computer based tools for eye examination has rarely been applied for general home use. The reason is that there is so much variability in screen size, pixel density, resolution, brightness, glare, aspect ratios, etc that it is extremely difficult to achieve consistency. Without consistency, there is no ability to make absolute measurements for most diagnoses or therapeutic prescriptions. By using a relative measurement over time, it allows for good results without absolute measurement.

Recommending the user to keep a consistent distance from the grid is important. This can be easily accomplished with easy to access items, such as a length of string or the length of one's arms. Each individual should be able to set their preferred distance to accommodate far-sightedness and to assure that the blind-spot fits appropriately within the grid surface.

Accelerating Detection of Changes to Vision

Recording the size and shape of the picture frame, together with date, and patient identifier enables the same shape to be retrieved and recreated at a later date for the same patient. For example, on an electronic screen. If upon a future review of the picture frame, the size of the affected area exceeds the size of the picture frame (ie: the affected area does not fit within the frame and distorts more than two adjacent lines), then one can conclude that the patient has suffered a change in vision; and should be referred to an eye care provider right away, before waiting for a next appointment.

Instructions for a preferred embodiment might proceed as:
Patient or helper is requested to stretch the four edges of a rectangle such that it surrounds the external perimeter of the affected area. (In instances where patient does not have confidence in manipulating the rectangle, then a limited menu of pre-shaped and pre-sized rectangles may provide an easier surrogate process for defining an apt frame size.)
Perimeter border lines should be moved as close as possible to the external perimeter of the affected area without distorting (as a result of the affected area of the retina)
A wandering gaze should only distort no more than two adjacent sides of the rectangle
Size & shape of the affected area is captured, along with other patient identifier information, date, etc
The initial measurement is considered a baseline, and should coincide with a recent visit to an eyecare professional (that is able to establish absolute vision measurements)
Future review of the picture frame rectangle will provide a comparison to the baseline benchmark
If, in the future, the affected area distorts more than two adjacent sides of the rectangle there is very strong evidence of a progression and growth of the retina disease, indicating the patient should return to their eye care professional right away, before the next scheduled office visit Border Quality The border of the picture frame separates the picture frame area from the balance of the grid. The inner portion of the frame should be maintained in a bright hue/color (preferably above the illuminance threshold) while the balance of the grid should be a relatively darker hue or shade. The line style that is used to create the perimeter (rectangular or other shape) can be enhanced.

The perimeter border lines should be differentiated from the other grid lines to help distinguish it from the grid and causing confusion. Having the perimeter border lines in bold and an adjacent parallel line helps accentuate distortion and simplify usage.

Using adjacent parallel lines with one bold and the other narrow helps accentuate distortion. When the lines are observed in close proximity to an affected area, the parallel lines distort. The distortion is accentuated in comparison to a single line because the two lines bleed together and the confluence of the lines is a highly visible "vee" shape. The higher visibility is the result of further darkening within the inside of the vee.

In one iteration, the bold line (=2 to 3× stroke of the conventional grid lines) has a secondary line of narrow stroke (=roughly ½ stroke of the conventional grid lines) separated by the width of the bold stroke line. Other iterations may have different stroke sizes and perhaps three or four lines. Other iterations may also include lines as described earlier—ie: dashed, of varying colors, etc.

Centerless Ease

Having a perimeter assessment tool relinquishes the importance of a center point. This reduces frustration and simplifies the use of the tool, especially for those who were unable or frustrated by attempting to fixate on a center point. With increased ease of use, regular adherence to a personal monitoring program is boosted.

Scalar Measurement

Having a perimeter defined provides the ability to measure the area within the perimeter to provide a scalar measurement regarding the size of affected area that is meaningful to a patient. This number can be correlated to the number and size of the boxes defined by a grid. In one example, each box could be considered a score of one, four or some divisible multiplier. If the perimeter was a simple rectangle that encircled a space 3 grid boxes high and 4 grid boxes wide, then 12 boxes would be surface area of the perimeter. A score of 12, 48 or some higher number would then be provided to the user.

Positional Measurement

Having a perimeter defined relative to some center point or defined relative within a total field of vision provides the patient with a way to describe the location of the spot to their family, friends, fellow patients or healthcare provider. For example, they may say that "I have a 12 unit loss in the Northwest corner of my vision."

Time Based Monitoring & Tracking

Having a scalar diagnostic measurement stored over time enables time-based monitoring and tracking. This ability to self-monitor and track one's progress over weeks and months is a great improvement over today's options. It also allows for historical reports to be generated that can provide detail of a patients testing activity over time.

Alert Systems

By using the time-based monitoring, systems can be established to alert a patient, a healthcare provider or other party in the event a user's vision has changed.

Monitoring Programs

Having a perimeter measurement provides users with a regular activity and report-out task. This activity can then be monitored by others to ensure the patient is in compliance with a monitoring regimen.

General Embodiments

The following descriptions show possible ways to apply the novel concepts within this document, but should not imply that they are the only way to execute the ideas.

The preferred embodiment will be an electronic tool driven by software application. It may be delivered as a piece of software, a client-server application or hosted centrally and available through the Internet.

The interface will be driven through an electronic display compatible with a computer or electronic device.

The preferred embodiment will enable, encourage and support the monitoring & self-diagnosing of peoples eyes and vision. It will be helpful for patients and non-patients. It will help patients address affected and unaffected eyes.

It will contain a grid that has several key features driven by the software:

Grid Lines
- Grid lines will include a variety of patterns (normal, dashed, dotted, bold stroke, etc)
- Grid lines will be discontinuously variable (flashing, pulsating, etc)
- Grid lines will have varying colors
- Grid line pattern, variability & color selection will be symmetrical when viewed in four directions emanating from the center (thus describing a box between four identical lines)
- Grid lines will be identified with unique number for each—similar to latitude & longitude lines Center Dot
- Center dot will be made obvious by color, flashing appearance or other attention getting visual cues Grid Customization
- Software will enable the users to select various colors, sizes, pattern types, center dot styles, dynamic styles (flashing, pulsating, no dynamics, etc) to meet their personal needs for clarity and visual diagnostic performance
- Software will enable users to alter background colors to enhance contrast or make their activity more pleasing to them
- Software will request users to finalize their check under a diverse spectrum of background colors, and multiple grid colors. This helps varying types of retinal disorders that are more noticeable in certain colors to become more apparent to the user at their earliest stages. For example, during the test, the background of the display will shift in color from white through yellow to red, then the grid color will shift from black to blue, and the background color will return from red through yellow back to white. The user may personally control the colors and manually step through the sequence as desired.

Driving Display Past the Illuminance Threshold
- For testing beyond the illuminance threshold, software will drive the screen to maximum brightness (typically bright white unless the user has selected another color for personal contrast improvement)
- Software will enable user to reduce brightness to prevent glare
- Software will interact with user to ensure that brightness exceeds the illuminance threshold by asking interactive questions to the user regarding their perception of their affected area
- Software will instruct the user that has not achieved the threshold to adjust their display's brightness, reduce the ambient lighting or wait until a darker time of day before proceeding
- This control ensures that people of all ages and visual status will be able to be served Picture Frame Perimeter Building
- Patient (or a helper) will be guided to view the grid with one eye covered
- User will manipulate a rectangle frame so that it surrounds the affected area
- Rectangular frame can be prepared in many ways: (Selecting from a menu of various sizes and shapes, dragging and dropping, manipulating through use of keystrokes, etc)
- By instructing the user to make the outer edge of the "frame" slightly larger than the affected area, a natural border perimeter is created that enables multiple benefits
  - Centerless relative positioning of the grid to assist stability of gaze
  - Ability to provide a firm "fence" around the affected area, enabling user to more rapidly detect subtle changes and gain very strong feedback if the affected area grows larger than the perimeter
  - Common language to describe one's condition
  - Relative positioning of the boxes (ie: 6 boxes in the northeast quadrant)

One Way the Software Might Control Making the "Picture Frame" Perimeter
- The software will ask the user to look at the grid with one eye closed (perhaps above the illuminance threshold or a high-contrast color)
- The user will then activate the perimeter line rectangle by clicking with a pointer
- The user will then be able to move each edge of the rectangle using arrow (or other) keys
- Each wall will be moved independently and separately until all four walls are moved and adjusted to the liking of the patient
- User will be able to continue editing the wall positions, or save the resulting size and shape Electronic Evaluation, Monitoring and Response
- Software will drive a scalar quantification of the size of the affected area, based upon the user's creation of "picture frame" rectangle around their affected area(s)
- For example the, picture frame should be just large enough to surround the affected area such that the perimeter lines are not distorted during a fixed gaze, and if the gaze does wander, no more than two adjacent sides (ie: east, west, north, south) should distort
- The scalar number may be equivalent to the actual number of boxes, a multiple of the boxes or in some descriptive word)
- Quantified result will be made available to the user and provide a very simple tool for communicating their condition to others (ie: "you received a score of 32)
- Quantified results will be displayed as a total aggregate or by sections (ie: 6 boxes in the northeast corner)
- Scalar measurement can be based upon whole grid boxes or fractions thereof.
- Software will manage storage of the scalar information (in a data repository managed locally, remotely, centrally, etc) for individual patients
- Stored data, when retrieved and compared will provide consistent monitoring
- Changes in results will signal possible change in eye health (through detecting changes in both the scalar value or size & shape of the picture frame over time)
- If a patient views a retrieved picture frame and their affected area distorts the lines of the perimeter, (more than two adjacent sides), then there is evidence of change in vision or eye health Limits can be set to accommodate slight variations in vision that occur from day to day, so that a hurdle level is established over which a user must pass in order to signal that the tests detect a change in vision Software can drive appropriate responses to changes in the affected area—for example:

Referral to one's eye care specialist

Redirection to a site selling eye-care related goods, services, etc

Offering educational materials on how to proceed

Storage of information will also be of great value to patients with memory loss

Health Management

Software can offer regular monitoring reminder communications to users to advise them to perform their monitoring on a regular basis Reminders can be keyed to adherence to a monitoring program so that communication is escalated when the user misses sessions Adherence can be linked to patient benefit programs enabling adjustments within a patients policy (ie: variable copays or rewards or compliance)

Preliminary studies have been conducted on an informal basis while formal university testing is being designed and funded. Conversations have resulted in the following anecdotes:

A) Interview with AMD Patient During Ophthalmic Evaluation by a Nurse:

As of this writing, one initial patient has been interviewed. 20 more patients will be interviewed later in 2007. The first patient tested was able to identify the shape and location of their scotoma on the inventor's grids within 3 seconds. This stood in stark contrast to the patient's inability after 60 seconds to identify the shape or location of their scotoma with the traditional Amsler grid.

B) Conversations with Retina Specialists, Opticians & Ophthalmic Technicians:

We have presented the VMS Grid test concepts to retina practices and ophthalmic practices in the geographic area of the inventor's home state. These informal reviews of early prototypes have garnered very positive feedback and encouragement. They have also provided further feedback regarding the inadequacy of current testing approaches. A retina specialist in Hartford, Conn. remarked: "I feel this will be of value to both wet and dry AMD patients—particularly those with unilateral AMD who often experience delays in presenting for diagnosis and treatment."

C) Conversations with AMD Patients:

We have presented the VMS test concepts to a small number of AMD patients. They have remarked that the tests are helpful to them and easier to understand and remember than their Amsler tests.

D) Conversation with RP Patient

We have presented the VMS test concepts to one individual with RP. He commented that the PC based grid did facilitate the objective monitoring of his RP. However, he cautioned that most early stage RP sufferers will not experience visual loss in proximity to the macula, the focus point of a typical test grid.

What is claimed is:

1. A visually stimulating grid system for monitoring and detecting retina issues which include, Age Related Macular Degeneration (AMD), comprising:

a static grid including:

major dimensions similar to those found in common Amsler Grids, wherein at least two of the lines that comprise the grid having enhancements to at least one of color, hue, brightness, line width, continuity, shape, or duplication, the at least two lines within the grid are distinguishably different from other lines in the grid, and the lines including enhancements are oriented to create a sequence comprising a continuous grid line adjacent to at least one discontinuous grid line, wherein each of said lines being one of a horizontal line or a vertical line, said sequence perceived as a pattern.

2. The visually stimulating grid system as in claim 1, wherein the characteristics of the at least two distinguishably different lines and the orientation of the distinguishably different lines establish a recognizable and memorable pattern that stimulates patients' memory and enables improved testing result recall during testing as well as after testing.

3. The visually stimulating grid system as in claim 1, wherein at least two of the lines are labeled by indicia to provide alpha numeric references denoting coordinates of said lines to enable patients to verbalize the results of their testing and improve record-keeping.

4. The visually stimulating grid system as in claim 1, wherein the luminance of the grid's test surface is raised relative to surrounding area in such a way as to exceed a patient's brain's cognitive ability to fill-in missing visual data associated with the patient's affected visual area and thereby make said affected visual area appear more visually prominent and thereby easier to recall during and after the test.

5. The visually stimulating grid system as in claim 1, wherein said discontinuous grid line comprises one of dashes, dots, combinations of dashes and dots or combinations of shaped line segments arranged to resemble dashes or dots.

6. The visually stimulating grid system as in claim 1, wherein the orientation of the distinguishably different lines is symmetrical in the four primary directions of up, down, left and right with respect to a centrally located dot within the grid thereby enhancing perception of a pattern.

7. A method for establishing an outer limit perimeter line around outer limits of a patient's existing affected area of visual impairment, including:

presenting a vision test for detecting an affected area of visual impairment;

establishing an outer limit of the affected area using vision tests, wherein, the vision tests include grid tests such that size and shape of said outer perimeter lines can be established as a surrogate for the actual size and shape of the affected area;

manipulating a position of movable perimeter lines so that they are immediately outside the affected area of visual impairment;

finding a scalar measurement value representing the size, shape and position of the perimeter lines;

recording and storing the scalar measurement value to enable a patient to self-monitor and track changes in vision;

comparing the scalar measurement with previously stored scalar measurements; and alerting patients' when the scalar measurements have exceeded a predetermined value.

8. The outer limit perimeter line method as claimed in claim 7, wherein the size and shape of the outer limit perimeter line test can be recreated during future testing enabling patients to answer a Boolean question regarding whether the affected area of vision still fits within the recreated outer perimeter line, and thereby accelerating detection of visual changes.

9. The outer limit perimeter line method as claimed in claim 7, wherein the perimeter is a pairing of at least two parallel lines that distorts in a more noticeable fashion as compared to a single line when viewed by a person with retina problems.

10. The outer limit perimeter line method as claimed in claim 7, wherein the surface area outside of the perimeter is shaded at a darker color and/or tone than the surface inside of the perimeter to facilitate recognition of when the affected area is either inside or outside of the outer limit perimeter line.

11. The outer limit perimeter line method as claimed in claim 7, wherein the outer limit perimeter line is a rectangle, and the 4 sides can be moved in or out relative to the center of the rectangle in such a way as to enable a patient to place each side immediately outside the outer limit of their affected visual area.

12. The outer limit perimeter line method as claimed in claim 7, wherein the luminance of a grid test surface is amplified relative to the surrounding area in such a way as to exceed a patient's brain's cognitive ability to fill-in missing visual data associated with the patient's area of affected vision and thereby make said affected area appear more visually prominent and thereby easier to test and monitor.

\* \* \* \* \*